(12) United States Patent
Xu et al.

(10) Patent No.: US 11,642,112 B2
(45) Date of Patent: May 9, 2023

(54) FLEXIBLE SURGICAL INSTRUMENT AND DRIVING UNIT THEREOF

(71) Applicant: BEIJING SURGERII TECHNOLOGY CO., LTD., Beijing (CN)

(72) Inventors: Kai Xu, Beijing (CN); Jiangran Zhao, Beijing (CN); Zhengchen Dai, Beijing (CN); Huichao Zhang, Beijing (CN); Huan Liu, Beijing (CN); Zenghui Liu, Beijing (CN); Zhixiong Yang, Beijing (CN); Zhijun Zhu, Beijing (CN)

(73) Assignee: BEIJING SURGERII TECHNOLOGY CO., LTD., Beijing (CN)

( * ) Notice: Subject to any disclaimer, the term of this patent is extended or adjusted under 35 U.S.C. 154(b) by 1107 days.

(21) Appl. No.: 16/329,752

(22) PCT Filed: Aug. 31, 2017

(86) PCT No.: PCT/CN2017/100021
§ 371 (c)(1),
(2) Date: Feb. 28, 2019

(87) PCT Pub. No.: WO2018/041231
PCT Pub. Date: Mar. 8, 2018

(65) Prior Publication Data
US 2019/0231331 A1    Aug. 1, 2019

(30) Foreign Application Priority Data

Aug. 31, 2016  (CN) .................. 201610797568.X
Aug. 31, 2016  (CN) .................. 201610799232.7

(51) Int. Cl.
*A61B 17/00* (2006.01)
*A61B 34/30* (2016.01)
*A61B 17/29* (2006.01)

(52) U.S. Cl.
CPC ........ *A61B 17/00234* (2013.01); *A61B 34/30* (2016.02); *A61B 2017/00314* (2013.01);
(Continued)

(58) Field of Classification Search
CPC combination set(s) only.
See application file for complete search history.

(56) References Cited

U.S. PATENT DOCUMENTS 5,792,135 A * 8/1998 Madhani ................ A61B 34/77
606/1
8,888,789 B2  11/2014 Prisco et al.
(Continued)

FOREIGN PATENT DOCUMENTS

CN  101572395 B  3/2011
CN  103085083 A  5/2013
(Continued)

OTHER PUBLICATIONS

European Patent Office, Supplementary European Search Report Issued in Application No. 17845533.3, dated Oct. 21, 2020, Germany, 6 pages.
(Continued)

*Primary Examiner* — Scott Luan
(74) *Attorney, Agent, or Firm* — McCoy Russell LLP

(57) ABSTRACT

Disclosed are a flexible surgical instrument and a driving unit thereof. The flexible surgical instrument may comprise a flexible continuous body structure composed of a distal structural body, a middle connecting body and a proximal structural body linked in sequence. The driving unit is linked to the flexible continuous body structure. When a structural
(Continued)

backbone driving mechanism in the driving unit drives the proximal structural body to turn in any direction, the distal structural body correspondingly turns in the opposite direction. A surgical end effector driving mechanism in the driving unit can drive a surgical end effector linked to the distal end of the distal structural body to implement the action control of the surgical end effector.

19 Claims, 10 Drawing Sheets

(52) U.S. Cl.
CPC ............... *A61B 2017/00323* (2013.01); *A61B 2017/00336* (2013.01); *A61B 2017/2932* (2013.01); *A61B 2034/301* (2016.02)

(56) References Cited

U.S. PATENT DOCUMENTS

| | | | |
|---|---|---|---|
| 2005/0096694 | A1 | 5/2005 | Lee |
| 2007/0043338 | A1 | 2/2007 | Moll et al. |
| 2009/0248042 | A1 | 10/2009 | Kirschenman |
| 2013/0090763 | A1 | 4/2013 | Simaan et al. |
| 2015/0352728 | A1* | 12/2015 | Wang ................... A61B 1/0057 74/490.04 |

FOREIGN PATENT DOCUMENTS

| | | |
|---|---|---|
| CN | 103315781 A | 9/2013 |
| CN | 103340707 A | 10/2013 |
| CN | 103340731 A | 10/2013 |
| CN | 103707322 A | 4/2014 |
| CN | 103948435 A | 7/2014 |
| CN | 104887313 A | 9/2015 |
| CN | 105751210 A | 7/2016 |
| CN | 106308939 A | 1/2017 |
| CN | 106361386 A | 2/2017 |
| EP | 1274480 B1 | 7/2006 |
| WO | 2009094670 A1 | 7/2009 |
| WO | 2015066536 A1 | 5/2015 |

OTHER PUBLICATIONS

European Patent Office, Extended European Search Report Issued in Application No. 17845533.3, dated Oct. 28, 2020, Germany, 21 pages.
Xu, K. et al., "Design of a Hyper-Redundant Continuum Manipulator for Intra-Cavity Tasks," Proceedings of the 2014 IEEE International Conference on Robotics and Biomimetics, Dec. 5, 2015, Bali, Indonesia, 6 pages.
Xu, K. et al., "Development of the SJTU Unfoldable Robotic System (SURS) for Single Port Laparoscopy," IEEE/ASME Transactions on Mechatronics, vol. 20, No. 5, Oct. 2015, 13 pages.
State Intellectual Property Office of the People's Republic of China, First Search Issued in Application No. 201610797568.X, dated Apr. 24, 2018, 3 pages.
State Intellectual Property Office of the People's Republic of China, First Search Issued in Application No. 201610799232.7, dated Jun. 12, 2018, 4 pages.
European Patent Office, Supplementary Partial European Search Report Issued in Application No. 17845533.3, dated Mar. 24, 2020, 7 pages.
ISA State Intellectual Property Office of the People's Republic of China, International Search Report Issued in Application No. PCT/CN2017/100021, dated Nov. 29, 2017, WIPO, 6 pages.

* cited by examiner

FLEXIBLE SURGICAL INSTRUMENT AND DRIVING UNIT THEREOF

CROSS REFERENCE TO RELATED APPLICATIONS

The present patent application is a U.S. national phase of Chinese International Application No. PCT/CN2017/100021 entitled "FLEXIBLE SURGICAL INSTRUMENT AND DRIVING UNIT THEREOF" and filed on Aug. 31, 2017. Chinese International Application No. PCT/CN2017/100021 claims priority to Chinese Patent Application No. 201610797568.X, filed on Aug. 31, 2016 and Chinese Patent Application No. 201610799232.7, filed on Aug. 31, 2016. The entire contents of each of the above-identified applications are hereby incorporated by reference for all purposes.

TECHNICAL FIELD

The present invention relates to a medical instrument, and in particular to a flexible surgical instrument.

BACKGROUND ART

In the single-port laparoscopic surgery and the natural orifice transluminal non-invasive surgery, all surgical instruments including a visual illumination module and a surgical manipulator have access to a surgical site through a single channel. A distal structure of a surgical instrument may consist of multiple rods hinged in series, and is driven by a pulling force from a steel wire rope, so that the surgical instrument can be turned at an articulated joint. Since the steel wire rope has to be continuously tensioned by a pulley, this driving method can hardly lead to further miniaturization of the surgical instrument, and also hardly lead to further improvement of the moving performance of the instrument.

SUMMARY OF THE INVENTION

According to an aspect of the invention, there is provided a flexible surgical instrument, comprising a flexible continuous body structure consisting of a distal structural body, a middle connecting body and a proximal structural body linked in sequence. A proximal end of the distal structural body being linked to the proximal structural body via the middle connecting body, and a distal end thereof being linked to a surgical end effector; the distal structural body consisting of at least one distal structural segment each comprising a distal fixing disk and structural backbones; and the proximal structural body comprises at least one proximal structural segment each comprising a proximal fixing disk, a proximal base disk and structural backbones. The flexible surgical instrument further comprises a driving unit linked to the flexible continuous body structure, the driving unit comprising: a driving segment fixing disk externally sheathed over and linked to the proximal fixing disk, a driving segment base plate externally sheathed over and linked to the proximal base disk, a driving segment connected between the driving segment fixing disk and the driving segment base plate and externally sheathed over the proximal structural body, a structural backbone driving mechanism fixed to the outside of the middle connecting body, and driving segment structural backbones with a middle section passing through the structural backbone driving mechanism and two ends passing through the driving segment base plate and then being respectively fixed onto the driving segment fixing disk, the number of the structural backbone driving mechanisms equalling to the number of the driving segment structural backbones. In this way, the structural backbone driving mechanisms implement the turning motion of the driving segment in any direction by cooperatively pushing and pulling the driving segment structural backbone, thereby implementing the turning motion of the proximal structural body in the same direction and the turning motion of the distal structural body in the opposite direction.

In an example, the driving unit further comprises: a second fixing end plate externally sheathed over and linked to a first fixing end plate of the middle connecting body, first structural backbone guide channels with one end being fixedly connected to the structural backbone driving mechanism and the other end being fixedly connected to the driving segment base plate, two or more feedback structural backbones, a part of each feedback structural backbone being arranged in the driving segment, and potentiometers equal in number to the feedback structural backbones. The structural backbone driving mechanisms are fixed onto the second fixing end plate, and the two ends of the driving segment structural backbone respectively pass through the first structural backbone guide channel; and two ends of each of the feedback structural backbones are respectively fixed onto the driving segment fixing disk and a slider in the respective potentiometer, the turning motion of the driving segment causes the change in length of the part of the feedback structural backbone that is located in the driving segment, the change in length causes the feedback structural backbone to push and pull the slider in the potentiometer such that the change in length is recorded by the potentiometer and the absolute turned shape of the driving segment is further obtained.

In a further example, the structural backbone driving mechanism comprises: two driving support plates and one first motor fixing plate arranged at intervals in sequence and integrally connected via a support column, a structural backbone driving motor mounted on the first motor fixing plate, a set of transmission gears and a set of pulleys rotatably arranged between the two driving support plates, and a driving gear connected to the structural backbone driving motor via a first coupling. In this way, the set of transmission gears and the set of pulleys respectively constitute several pull-gear assemblies, the pulley and the gear of each of the pulley-gear assemblies are coaxially and fixedly connected, and the gears mesh with each other; and the driving segment structural backbone extends between the pulleys of the pulley-gear assemblies through the first structural backbone guide channel, the driving gear meshes with the gear of one of the pulley-gear assemblies to transmit a driving force, the set of transmission gears and the set of pulleys rotate together about their respective axes, thereby pushing and pulling the driving segment structural backbone by means of frictional forces, and the first structural backbone guide channel is fixedly connected to the support column at one end and is fixedly connected to the driving segment base plate at the other end.

In a yet further example, the middle connecting body comprises a first fixing end plate and second structural backbone guide channels, the second structural backbone guide channels being fixed onto the first fixing end plate at one end and being fixed onto the proximal base disk at the other end; and the structural backbones on the distal structural segment are securely connected, in one-to-one correspondence, to or are the same as the structural backbones on the proximal structural segment, and one end of the structural backbone is securely connected to the proximal fixing disk, and the other end thereof passes through the second structural backbone guide channel and is then securely connected to the distal fixing disk.

In a still further example, the driving unit further comprises a transmission mechanism disposed within the middle connecting body, the transmission mechanism comprising: a guide block and a transmission spacing disk fixed onto the proximal base disk via the support column, a connection block running through a central hole of the guide block and movable back and forth in the central hole of the guide block, a actuation wire guide channel with two ends being respectively fixed onto the first fixing end plate and the transmission spacing disk, a actuation wire with one end passing through the actuation wire guide channel and the central hole of the transmission spacing disk in sequence and then being fixed onto the connection block, and the other end passing through the center of the first fixing end plate to extend into and then extend along with the distal structural body and finally being fixed onto the surgical end effector, and a first magnet fixed onto the connection block.

In a still further example, the driving unit further comprises a surgical end effector driving mechanism, the surgical end effector driving mechanism comprising: a connection frame configured to be linked to a multi-degree-of-freedom robotic arm, a second motor fixing plate, a support plate and a bevel gear box mounted on the connection frame, a surgical end effector driving motor mounted on the second motor fixing plate, a pair of transmission gears rotatably arranged on the support plate, a sliding groove jacket mounted on the bevel gear box, a threaded rod located within the sliding groove jacket and coaxially fixed to an output end of the bevel gear box, a nut in threaded fit with the threaded rod, two sliding blocks arranged spaced apart from each other in the sliding groove jacket and capable of sliding back and forth, an anti-rotation slider securely connected to one of the two sliding blocks, a second magnet mounted on the front end of the other of the two sliding blocks, and a spring with two end being fixedly connected to the two sliding blocks, respectively. The surgical end effector driving motor drives the threaded rod to rotate by means of a second coupling, the pair of transmission gears and the bevel gear box, and an input gear of the pair of transmission gears is coaxially fixed to the second coupling and an output gear thereof is coaxially fixed to an input end of the bevel gear box; under the action of the anti-rotation slider, the threaded rod rotationally drives the nut and the sliding block to slide back and forth under the guidance of a lateral groove of the sliding groove jacket; the second magnet is coupled with the first magnet to transmit a push-pull motion, thereby implementing the motion control of the surgical end effector; and the spring causes the nut to output a stable and controllable pushing or pulling force to the actuation wire within a limited sliding travel, preventing the surgical end effector from generating an excessive snap force.

In a still further example, the flexible surgical instrument is able to be mounted on an end disk of the multi-degree-of-freedom robotic arm via the connection frame, and the multi-degree-of-freedom robotic arm comprises four or more joints, the joints being able to implement the overall lateral deflection and the overall feed freedom of the flexible surgical instrument with a surgical site incision point as the fixed point, and able to implement the overall rotation freedom of the flexible surgical instrument about its own axis.

In a still further example, the distal structural segment further comprises a bellows and a bellows connection plate; the structural backbones of the distal structural segment pass through structural backbone passage holes distributed in several sections of the bellows, and have front ends thereof fixed onto the distal fixing disk; the distal end of the bellows section at the most distal end is securely connected to the distal fixing disk, the proximal end of the bellows section at the most proximal end is connected to the front end of the structural backbone guide channels in the middle connecting body, and the remaining ends of the bellows sections are all securely connected to the bellows connection plate; and a plurality of actuation wire spacing disks are further distributed at intervals in each of the bellows sections, and the actuation wire of the surgical end effector passes through the center of each of the actuation wire spacing disks in sequence.

In a still further example, the distal structural segment further comprises a plurality of distal spacing disks distributed at intervals between the distal fixing disk and the middle connecting body, and the structural backbones of the distal structural segment pass through structural backbone passage holes distributed in each of the distal spacing disks, and have the front ends thereof fixed onto the distal fixing disk; the actuation wire of the surgical end effector passes through the center of each of the distal spacing disks in sequence; the proximal structural segment further comprises a plurality of proximal spacing disks distributed at intervals between the proximal fixing disk and the proximal base disk, and the structural backbones of the proximal structural segment have one end thereof fixed onto the proximal fixing disk and the other end thereof pass through structural backbone passage holes distributed in the proximal spacing disks in sequence, and are then securely connected, in one-to-one correspondence, to or are the same as the structural backbones of the distal structural segment; and the driving unit further comprises a plurality of driving segment spacing disks distributed at intervals between the driving segment base plate and the driving segment fixing disk, and the two ends of the driving segment structural backbone respectively pass through the first structural backbone guide channel, then pass through the driving segment base plate and the driving segment spacing disks in sequence, and are respectively fixed onto the driving segment fixing disk.

In a still further example, the structural backbones of the distal structural segment and/or the structural backbones of the proximal structural segment are elastic elongated rods or elongated tubes made of a nickel titanium alloy or stainless steel; in the case of using a plurality of distal structural segments or a plurality of proximal structural segments, if the structural backbones of a preceding distal structural segment or proximal structural segment use elastic elongated tubes, the structural backbones of the next distal structural segment or proximal structural segment are able to pass through the elastic elongated tubes or directly pass through the structural backbone passage holes in the distal spacing disks or in the proximal spacing disks; and the number of the structural backbones of each of the distal structural segments or the proximal structural segments is three or more.

In a still further example, an outside of the distal structural body is coated with a flexible envelope and a rigid pre-bent sleeve in sequence from the inside to the outside, the sleeve passes through a sheath fixed to a skin incision, the sheath provides a channel for instruments required for a single-port laparoscopic surgery, and the channel is an oblique channel and does not limit the lateral rotational motion of the flexible surgical instrument about a particular fixed point.

In a still further example, an outside of the distal structural body is coated with a flexible envelope and a rigid straight sleeve in sequence from the inside to the outside.

The sleeve passes through a sheath including only one channel, and the sheath is fixed to a skin incision.

In a still further example, the number of the proximal structural segments is equal to the number of the distal structural segments.

According to another aspect of the present invention, provided is a driving unit for driving a flexible continuous body structure, the driving unit comprising: a driving segment fixing disk externally sheathed over and linked to a proximal fixing disk of a proximal structural body in the flexible continuous body structure, a driving segment base plate externally sheathed over and linked to the proximal base disk of the proximal structural body, a driving segment connected between the driving segment fixing disk and the driving segment base plate and externally sheathed over the proximal structural body, driving segment structural backbones with two ends passing through the driving segment base plate and then being respectively fixed onto the driving segment fixing disk, and structural backbone driving mechanisms through which a middle section of the driving segment structural backbone passes, the number of the structural backbone driving mechanisms equalling to the number of the driving segment structural backbones. The structural backbone driving mechanisms implement the turning motion of the driving segment in any direction by cooperatively pushing and pulling the driving segment structural backbone, thereby implementing the turning motion of the proximal structural body in the same direction.

In an example, the driving unit further comprises: a second fixing end plate externally sheathed over and linked to a first fixing end plate of a middle connecting body in the flexible continuous body structure, first structural backbone guide channels with one end being fixedly connected to the structural backbone driving mechanism and the other end being fixedly connected to the driving segment base plate, two or more feedback structural backbones, a part of each feedback structural backbone being arranged in the driving segment, and potentiometers equal in number to the feedback structural backbones. The structural backbone driving mechanisms are fixed onto the second fixing end plate, and the two ends of the driving segment structural backbone respectively pass through the first structural backbone guide channel; and two ends of each of the feedback structural backbones are respectively fixed onto the driving segment fixing disk and a slider in the respective potentiometer.

In a further example, the structural backbone driving mechanism comprises: two driving support plates and one first motor fixing plate arranged at intervals in sequence and integrally connected via a support, a structural backbone driving motor mounted on the first motor fixing plate, a set of transmission gears and a set of pulleys rotatably arranged between the two driving support plates, and a driving gear connected to the structural backbone driving motor via a first coupling. The set of transmission gears and the set of pulleys respectively constitute several pull-gear assemblies, the pulley and the gear of each of the pulley-gear assemblies are coaxially and fixedly connected, and the gears mesh with each other; and the driving segment structural backbone extends between the pulleys of the pulley-gear assemblies through the first structural backbone guide channel, the driving gear meshes with the gear of one of the pulley-gear assemblies to transmit a driving force, the set of transmission gears and the set of pulleys rotate together about their respective axes, thereby pushing and pulling the driving segment structural backbone by means of frictional forces, and the first structural backbone guide channel is fixedly connected to the support column at one end and is fixedly connected to the driving segment base plate at the other end.

In a still further example, the driving unit further comprises a transmission mechanism disposed within the middle connecting body, the transmission mechanism comprising: a guide block and a transmission spacing disk fixed onto the proximal base disk, a connection block running through a central hole of the guide block and movable back and forth in the central hole of the guide block, a actuation wire guide channel with two ends being respectively fixed onto the first fixing end plate and the transmission spacing disk, a actuation wire with one end passing through the actuation wire guide channel and the central hole of the transmission spacing disk in sequence and then being fixed onto the connection block, and the other end passing through the center of the first fixing end plate to extend into and then extend along with a distal structural body of the flexible continuous body structure and finally being fixed onto the surgical end effector at the distal end of the distal structural body, and a first magnet fixed onto the connection block.

In a still further example, the driving unit further comprises a surgical end effector driving mechanism, the surgical end effector driving mechanism comprising: a motor drive assembly, a bevel gear box connected to an output end of the motor drive assembly, a sliding groove jacket mounted on the bevel gear box, a linear transmission assembly located within the sliding groove jacket and connected to an output end of the bevel gear box, two sliding blocks arranged spaced apart from each other in the sliding groove jacket and capable of sliding back and forth, one of the two sliding blocks being connected to a movable end of the linear transmission assembly, a second magnet mounted on the other of the two sliding blocks, and a spring with two end being fixedly connected to the two sliding blocks, respectively. The motor drive assembly transmits power to the linear transmission assembly through the bevel gear box and the linear transmission assembly drives the sliding block connected thereto to slide back and forth under the guidance of a lateral groove of the sliding groove jacket; the second magnet is coupled with the first magnet to transmit a push-pull motion, thereby implementing the motion control of the surgical end effector; and the spring causes the linear transmission assembly to output a stable and controllable pushing or pulling force to the actuation wire within a limited sliding travel, preventing the surgical end effector from generating an excessive snap force.

In a still further example, the motor drive assembly comprises: a connection frame for mounting the bevel gear box, a second motor fixing plate and a support plate mounted on the connection frame, a surgical end effector driving motor mounted on the second motor fixing plate, and a pair of transmission gears rotatably arranged on the support plate. An input gear of the pair of transmission gears is coaxially connected to an output shaft of the surgical end effector driving motor via a second coupling, and an output gear of the pair of transmission gears is coaxially connected to an input end of the bevel gear box.

In a still further example, the linear transmission assembly comprises: a threaded rod located within the sliding groove jacket and coaxially connected to the output end of the bevel gear box, and a nut in threaded fit with the threaded rod. The nut is the movable end of the linear transmission assembly, which is securely connected to one of the two sliding blocks via an anti-rotation slider.

By using a flexible continuous body structure comprising a proximal structural body, a middle connecting body and a distal structural body as the main body, and in combination with a driving unit which comprises a driving segment linked to the proximal structural body, and can cause the driving segment together with the proximal structural body to turn in any direction, the flexible surgical instrument provided in the embodiments of the present invention can implement the turning motion of the distal structural body in any direction, and in turn can implement the motion control of the surgical end effector located at the distal end of the distal structural body.

DETAILED DESCRIPTION OF EMBODIMENTS

The technical solutions of the embodiments of the present application will be clearly and completely described below in conjunction with the accompanying drawings of the embodiments of the present application; and obviously, the embodiments described are merely some of, rather than all, the embodiments of the present application. On the basis of the embodiments of the present application, all the other embodiments obtained by those skilled in the art without any inventive effort shall fall within the scope of protection of the present application.

Figure 1:
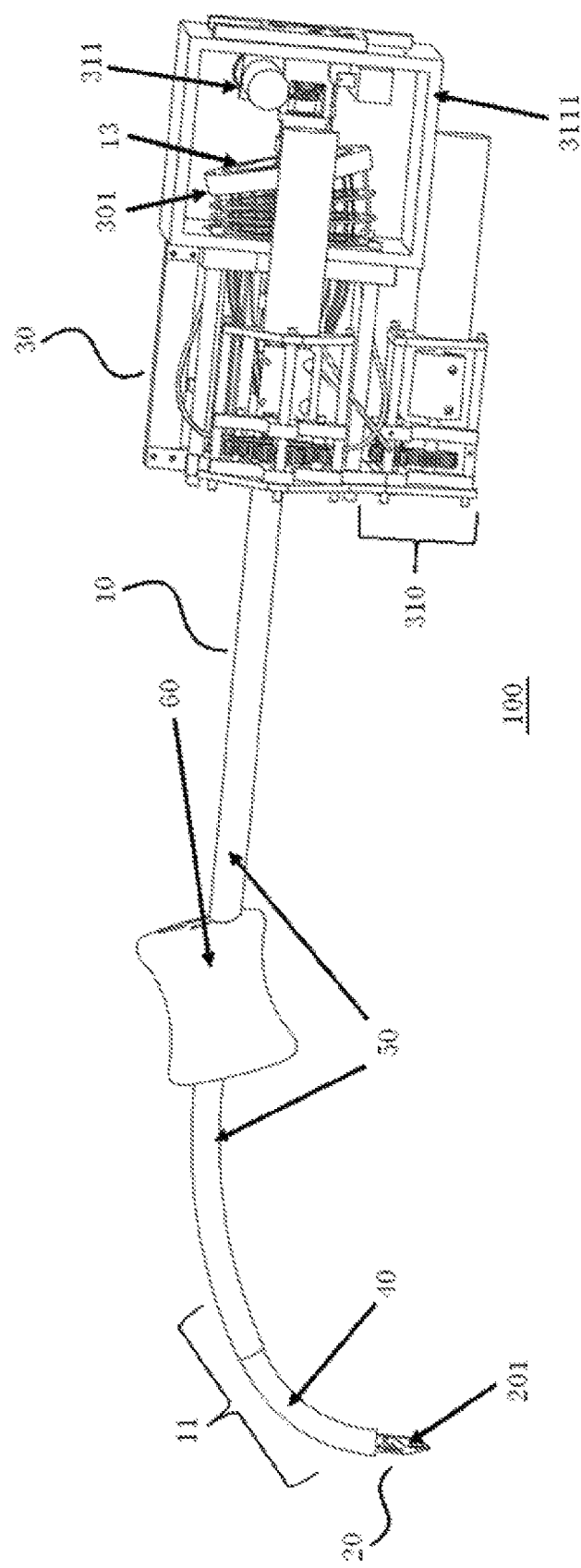
FIG. 1 is an overall structural schematic diagram of a flexible surgical instrument in accordance with an example of the present invention.

FIG. 1 illustrates a flexible surgical instrument 100 provided according to an embodiment of the present invention, which flexible surgical instrument may comprise a flexible continuous body structure 10, a surgical effectuation unit 20 and a driving unit 30. Hereinafter, for a component, the distal end refers to the end of the component that is remote from a surgical operator but close to a surgical site, and may also be referred to as the front end; and the proximal end refers to the end of the component that is close to the operator but away from the surgical site, and may also be referred to as the rear end.

The flexible continuous body structure 10 may comprise a distal structural body 11, a middle connecting body 12 and a proximal structural body 13 linked in sequence. The driving unit 30 is linked to the proximal structural body 13. A surgical end effector 201 in the surgical effectuation unit 20 is linked to the front end of the distal structural body 11. When a structural backbone driving mechanism 310 in the driving unit 30 drives the proximal structural body 13 to turn in any direction, the distal structural body 11 can correspondingly turn in the opposite direction. A surgical end effector driving mechanism 311 in the driving unit 30 can drive the surgical end effector 201 at the front end of the distal structural body 11 to implement the action control of the surgical end effector 201.

Figure 2:
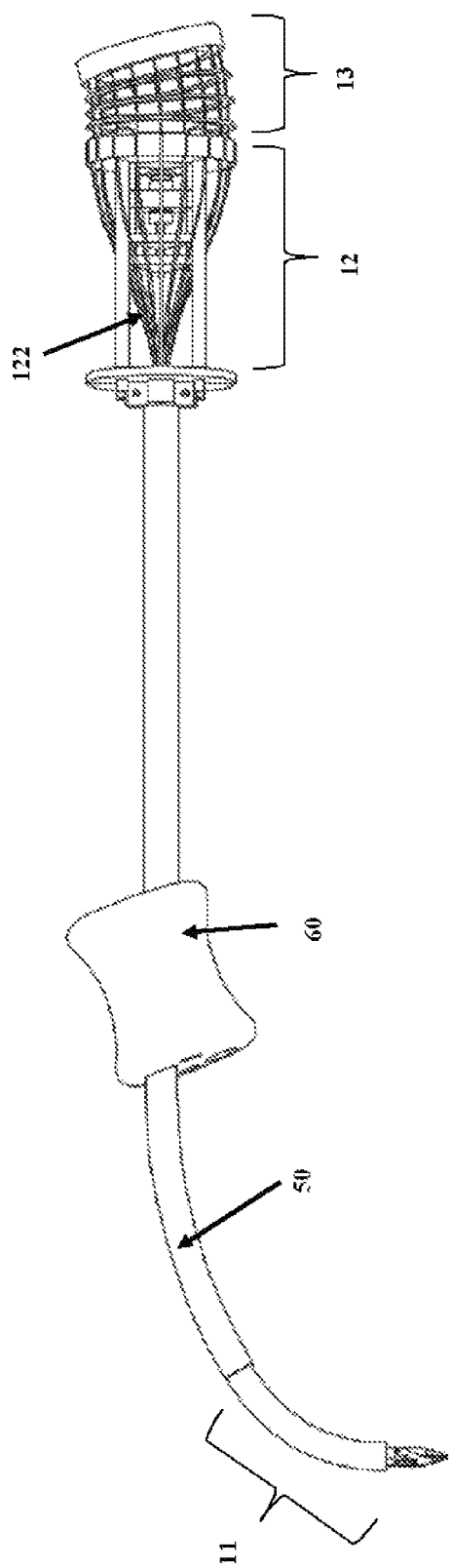
FIG. 2 is a structural schematic diagram of a flexible body structure passing through a multi-hole sheath in accordance with an example of the present invention.

As shown in FIG. 2, the distal structural body 11 is an elongated flexible structure with one end being linked to the proximal structural body 13 via the middle connecting body 12 and the other end being linked to the surgical end effector 201. The distal structural body 11 may be of a structure including a bellows 112, or a structure including a plurality of spacing disks distributed at intervals. The two forms of structures of the distal structural body 11 will be respectively described below.

Figure 3A:
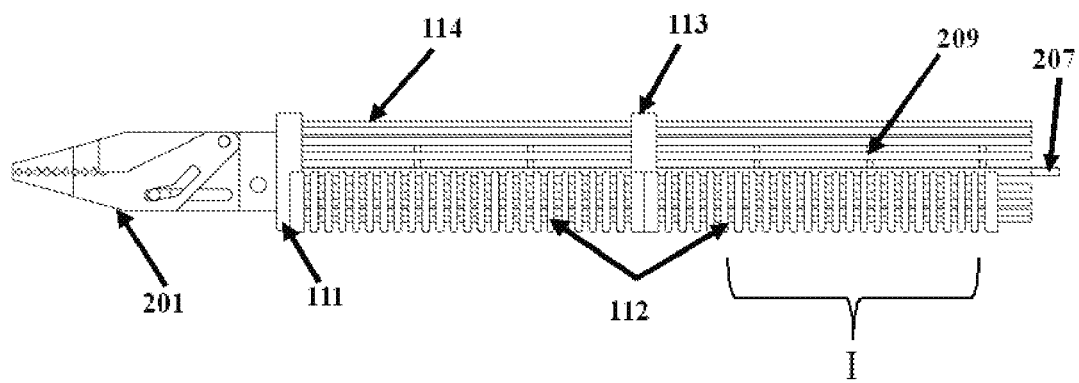
FIG. 3A is a partial sectional view of a distal structural body including a bellows in accordance with an example of the present invention.
Figure 3B:
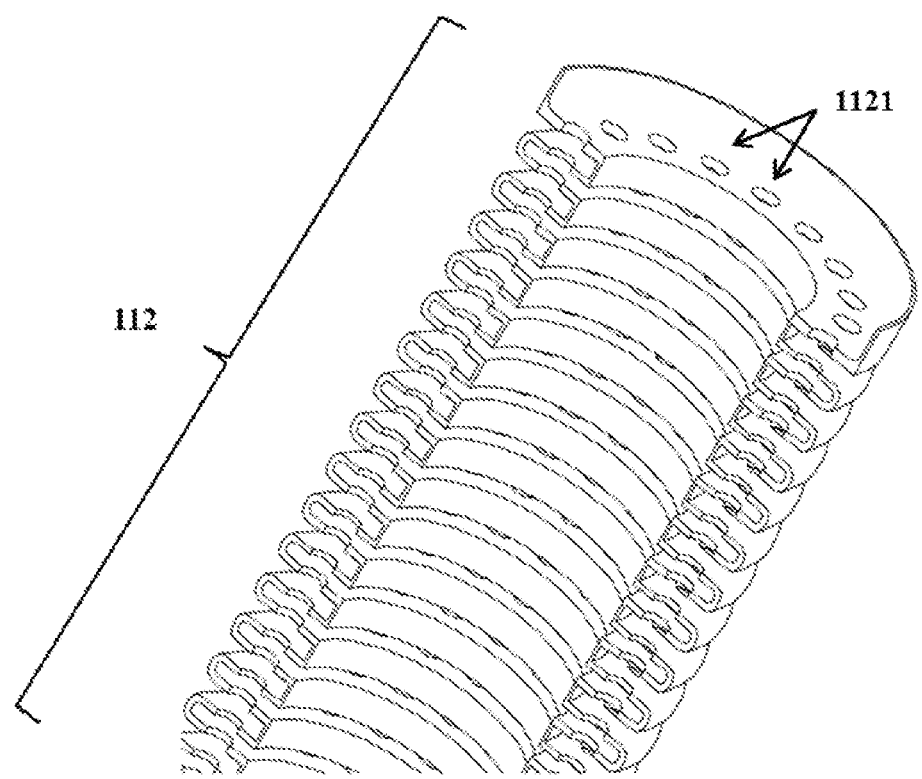
FIG. 3B is a structural schematic diagram of the bellows shown in FIG. 3A.

As shown in FIGS. 3A and 3B, the distal structural body 11 including the bellows 112 is composed of at least one distal structural segment I. Each of the distal structural segments I comprises a distal fixing disk 111, several bellows sections 112 (two in the present embodiment, but the invention is not limited thereto), a bellows connection plate 113, and a plurality of distal structural backbones 114 (eighteen in this embodiment, but the invention is not limited thereto). The distal structural backbones 114 pass through structural backbone passage holes distributed in the bellows 112, and the front ends thereof are fixed onto the distal fixing disk 111. The distal end of the bellows section 112 at the most distal end is securely connected to the distal fixing disk 111; the proximal end of the bellows section 112 at the most proximal end is connected to the distal end of a second structural backbone guide channel in the middle connecting body 12, the connection may be at anywhere on an axis of an outer sleeve 50; and the remaining ends of the bellows sections 112 are all securely connected to the bellows connection plate 113. The bellows 112 can be bent in any direction, and the structural backbone passage holes 1121 therein can be used to prevent the distal structural backbone 114 from being destabilized when being pushed and pulled.

Figure 4:
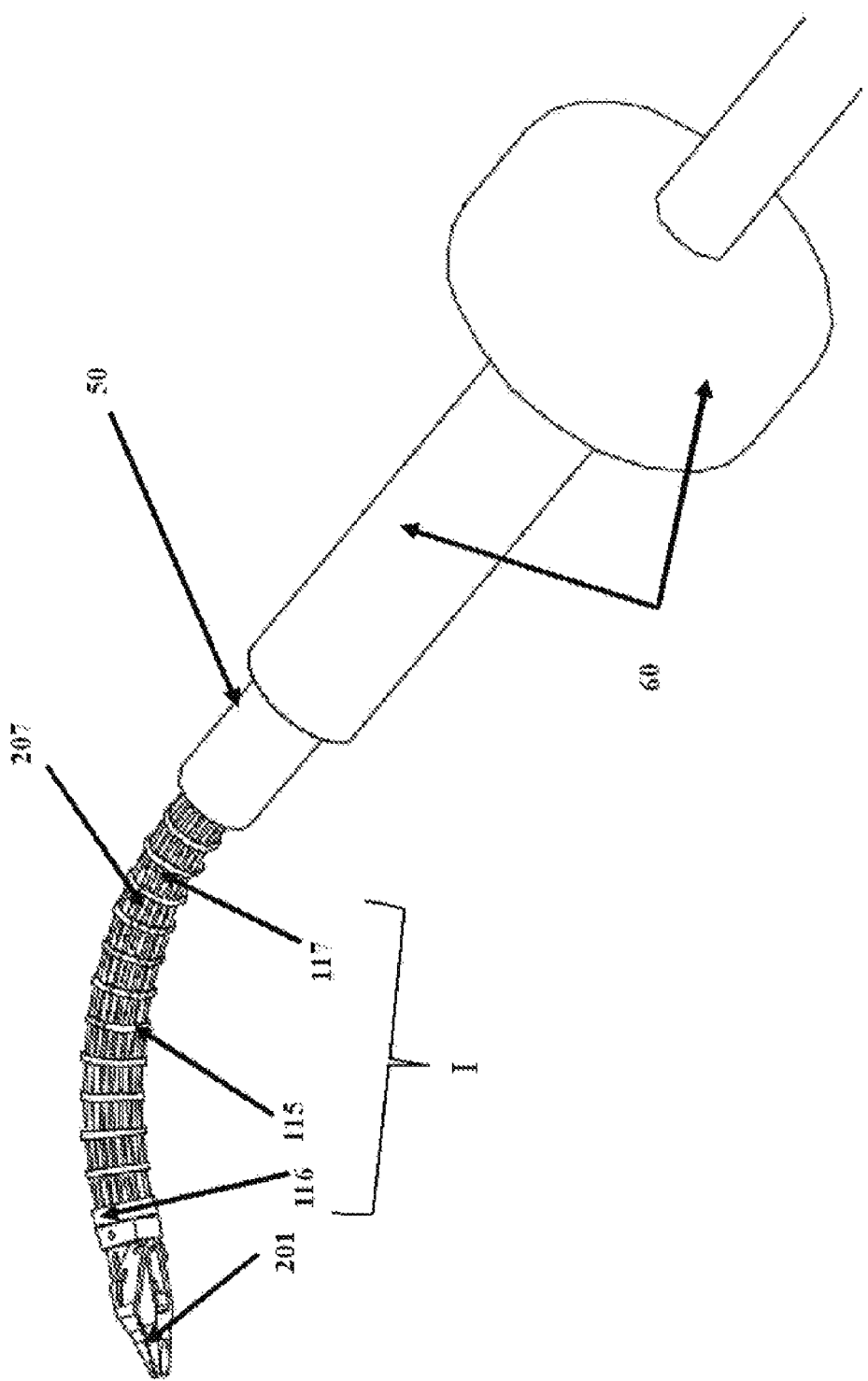
FIG. 4 is a structural schematic diagram of a distal structural body using a plurality of spacing disks distributed at intervals in accordance with an embodiment of the present invention.

As shown in FIG. 4, the distal structural body 11 including a plurality of distal spacing disks 115 distributed at intervals is also composed of at least one distal structural segment I. Each of the distal structural segments I comprises several distal spacing disks 115, a distal fixing disk 116 and a plurality of distal structural backbones 117. The number of distal spacing disks 115 are distributed at intervals between the distal fixing disk 116 and the middle connecting body 12. The plurality of distal structural backbones 117 pass through structural backbone passage holes distributed in the number of distal spacing disks 115, and have the front ends thereof fixed onto the distal fixing disk 116. The distal spacing disks 115 function to prevent the distal structural backbones 117 from being destabilized when being pushed and pulled.

Figure 5:
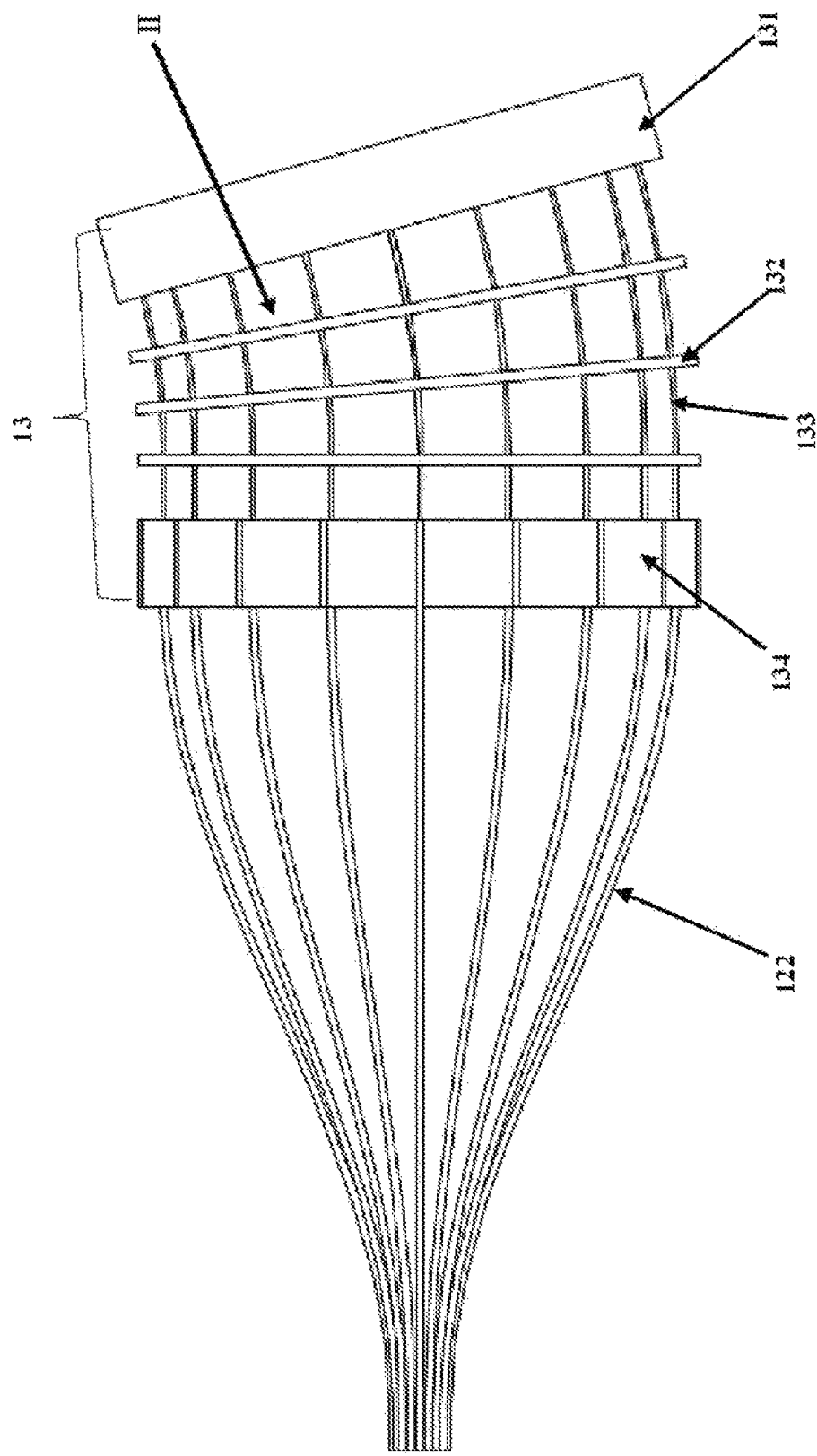
FIG. 5 is a structural schematic diagram of a proximal structural body in accordance with an example of the present invention.
Figure 7:
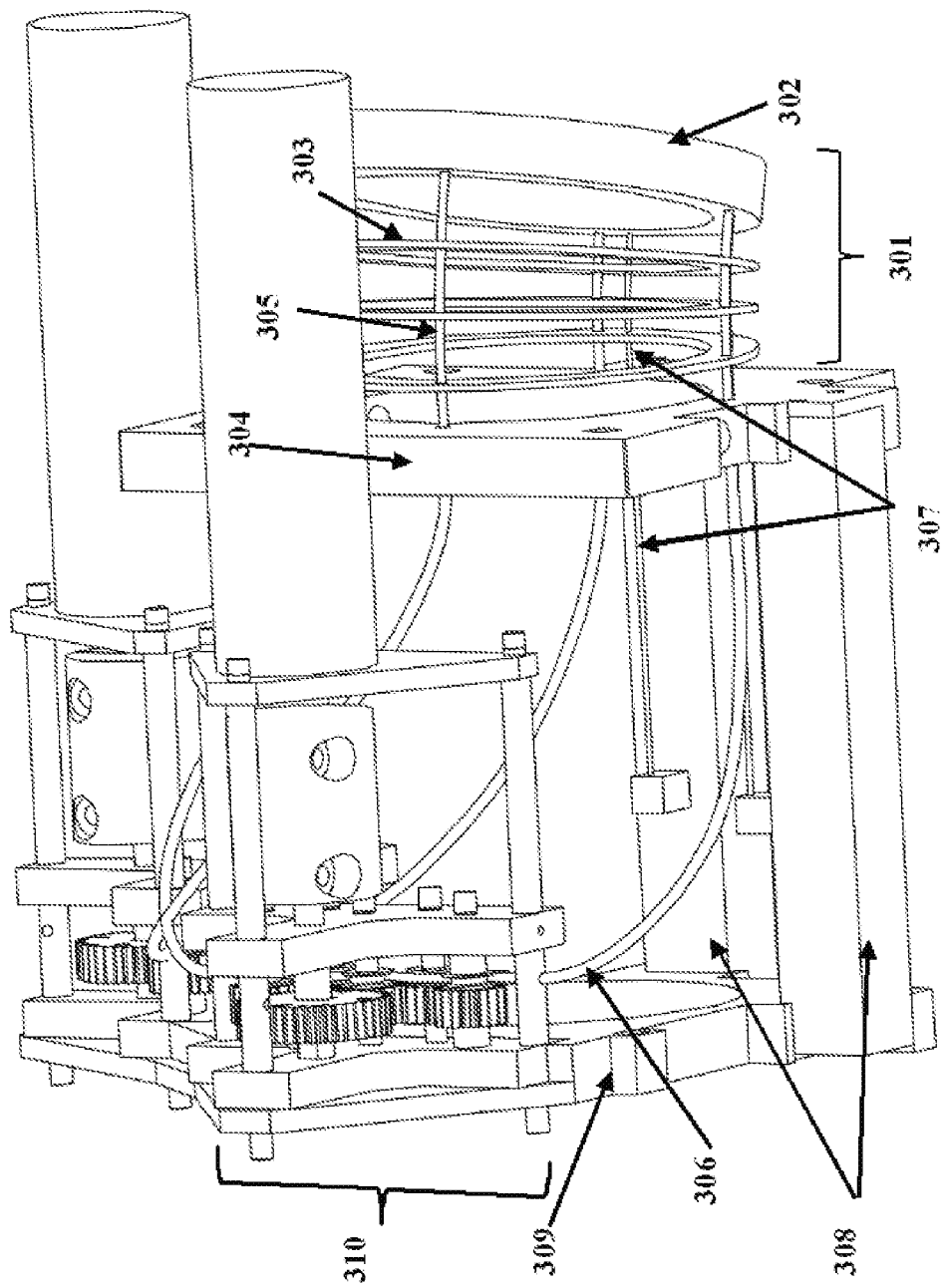
FIG. 7 is a structural schematic diagram of a driving unit in accordance with an example of the present invention.

As shown in FIGS. 1, 5 and 7, the proximal structural body 13 and a driving segment 301 in the driving unit 30 are of ring-shaped structures nested inside each other, the proximal structural body 13 is composed of at least one proximal structural segment II, and the number of the proximal structural segments II may be consistent with the number of the distal structural segments I. Each of the proximal structural segments II may comprise a proximal fixing disk 131, several proximal spacing disks 132, proximal structural backbones 133 and a proximal base disk 134, and the number of the proximal structural backbones 133 may be consistent with the number of the distal structural backbones 114 or 117. The number of proximal spacing disks 132 are distributed at intervals between the proximal fixing disk 131 and the proximal base disk 134, and function to prevent the proximal structural backbones 133 from being destabilized when being pushed and pulled. The proximal structural backbones 133 in the proximal structural segment II may be securely connected, in one-to-one correspondence, to or are the same as the distal structural backbones 114 or 117 in the distal structural segment I. In this way, one end of each of the plurality of structural backbones 133, 114 or 117 is fixed onto the proximal fixing disk 131, and the other end thereof passes through the respective one of the structural backbone passage holes distributed in the proximal spacing disk 132, is guided by the middle connecting body 12 to extend into the distal structural body 11, passes through the respective one of the structural backbone passage holes distributed in the distal spacing disk 115 or the bellows 112, and is then fixed onto the distal fixing disk 116. By driving the proximal fixing disk 131 to turn in any direction, it is possible to drive the distal structural body 11 to turn in the opposite direction in a certain proportional relationship. The proportional relationship may be determined jointly by the distribution radii of the proximal structural backbones 133 and the distal structural backbones 114, 117.

In one embodiment, the distal structural backbones 114, 117 and the proximal structural backbones 133 may be elastic elongated rods or elongated tubes, and may be made of a material such as a nickel titanium alloy or stainless steel. In the case of using the plurality of distal structural segments I or the plurality of proximal structural segments II, if the structural backbones of a preceding distal structural segment I or proximal structural segment II use elastic elongated tubes, the structural backbones of the next distal structural segment I or proximal structural segment II can pass through the elastic elongated tubes or directly pass through the structural backbone passage holes in the distal spacing disks 115, the bellows 112 or the proximal spacing disks 132. In this way, further miniaturization can be achieved without changing the relative motion relationship of the various structural segments in the proximal structural body 13. For each of the distal structural segments I or the proximal structural segments II, the number of the structural backbones therein may be three or more. The redundant arrangement of the structural backbones (the number thereof being greater than three) in the proximal structural body, the middle connecting body and the distal structural body can effectively improve the safety, reliability and load capacity of the instrument.

Figure 6:
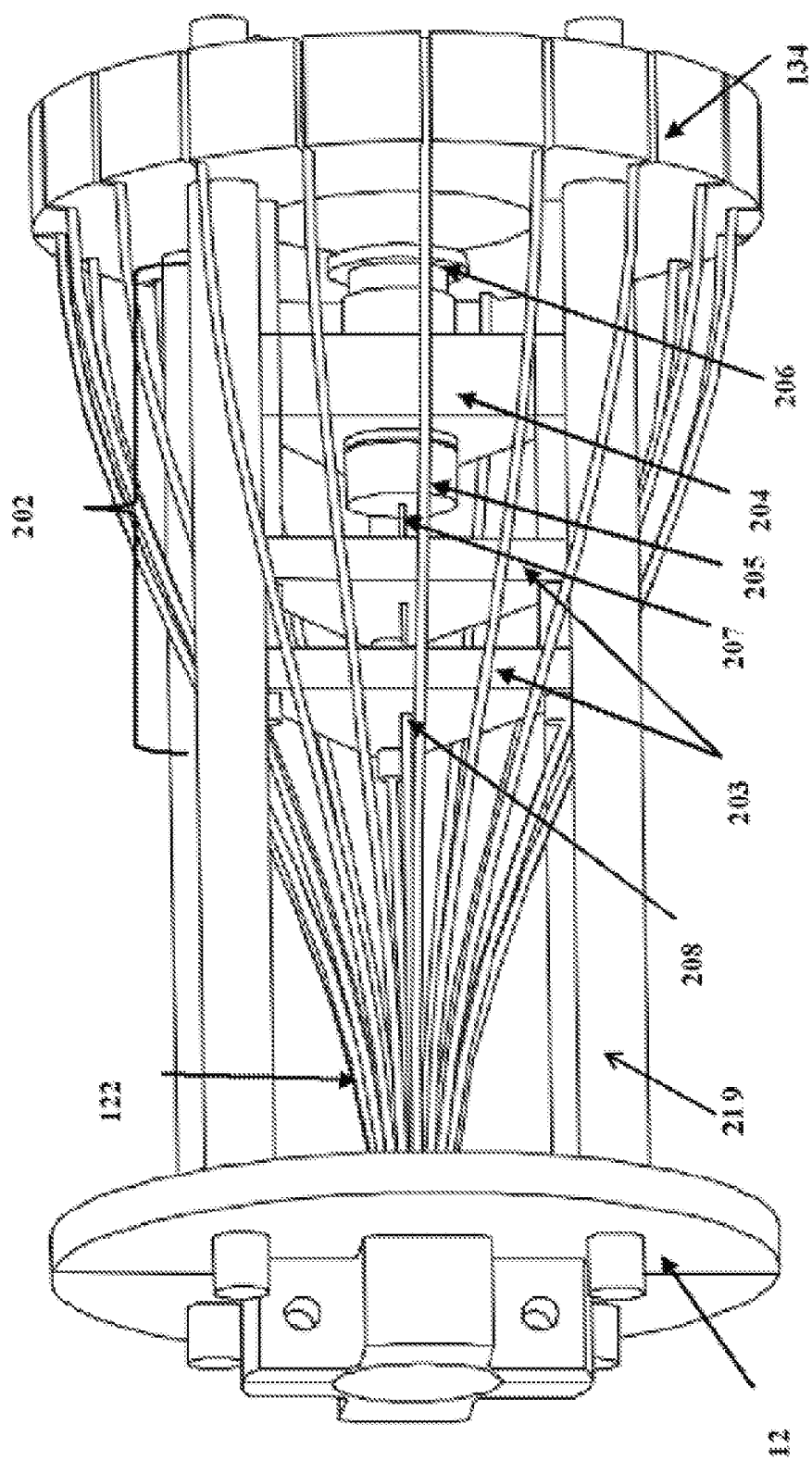
FIG. 6 is a structural schematic diagram of a middle connecting body and a transmission mechanism in accordance with an example of the present invention.

As shown in FIG. 6, the middle connecting body 12 may comprise a first fixing end plate 121 and second structural backbone guide channels 122. The second structural backbone guide channels 122 are bundled and fixed onto the first fixing end plate 121 at one end, and are fixed onto the proximal base disk 134 of the proximal structural body 13 at the other end, for guiding the structural backbones to maintain the shape of the structural backbones under a pushing or pulling force. Therefore, the number of the second structural backbone guide channels 122 should be equal to the number of the structural backbones. The second structural backbone guide channels 122 may be of a sleeve structure as shown in FIG. 6, or any other structural form, such as a multi-cavity structure, that can prevent the deformation of the structural backbones under a pushing or pulling force.

As shown in FIGS. 1, 4 and 6, the surgical effectuation unit 20 may comprise a surgical end effector 201 linked to the front end of the distal structural body 11 and a transmission mechanism 202 disposed within the middle connecting body 12. The transmission mechanism 202 may comprise several transmission spacing disks 203 (illustrated as two, but the present invention is not limited thereto), a guide block 204, a connection block 205, a first magnet 206, a actuation wire 207, and a actuation wire guide channel 208. The transmission spacing disks 203 and the guide block 204 may be fixed onto the proximal base disk 134 of the proximal structural body 13 via support columns 219. The connection block 205 can run through a central hole of the guide block 204 and can move back and forth in the central hole of the guide block 204. Two ends of the actuation wire guide channel 208 are respectively fixed onto the first fixing end plate 121 and the transmission spacing disks 203. One end of the actuation wire 207 passes through the actuation wire guide channel 208, then passes through central holes of the transmission spacing disks 203, and is fixed onto the connection block 205. The transmission spacing disks 203 function to prevent the actuation wire 207 from being destabilized when being pushed and pulled. The other end of the actuation wire 207 passes through the center of the first fixing end plate 121 of the middle connecting body 12, extends into and then extends along with the distal structural body 11, and is finally fixed onto the surgical end effector 201. The first magnet 206 is fixed onto the connection block 205, which can push and pull the actuation wire 207 by pushing and pulling the connection block 205, thereby implementing the action control of the mechanical surgical end effector 201 (such as surgical forceps). It should be understood by those skilled in the art that the actuation wire 207 can also transmit energy, such as electric energy and ultrasonic vibration, to an electrosurgical surgical end effector 201 (such as an electric knife and an ultrasonic knife) so as to perform an electrosurgical operation.

In one embodiment, as shown in FIG. 3A, when the distal structural body 11 including the bellows 112 is used, a plurality of actuation wire spacing disks 209 may be distributed at intervals in each of the bellows sections 112. In this way, the actuation wire 207 can pass through the center of each of the actuation wire spacing disks 209 in sequence, and the actuation wire spacing disks 209 function to prevent the actuation wire 207 from being destabilized when being pushed and pulled. When the distal structural body 11 including the plurality of distal spacing disks 115 distributed at intervals is used, the actuation wire 207 passes through the center of each of the distal spacing disks 115 in sequence, and the distal spacing disks 115 can also prevent the actuation wire 207 from being destabilized when being pushed and pulled.

Figure 9:
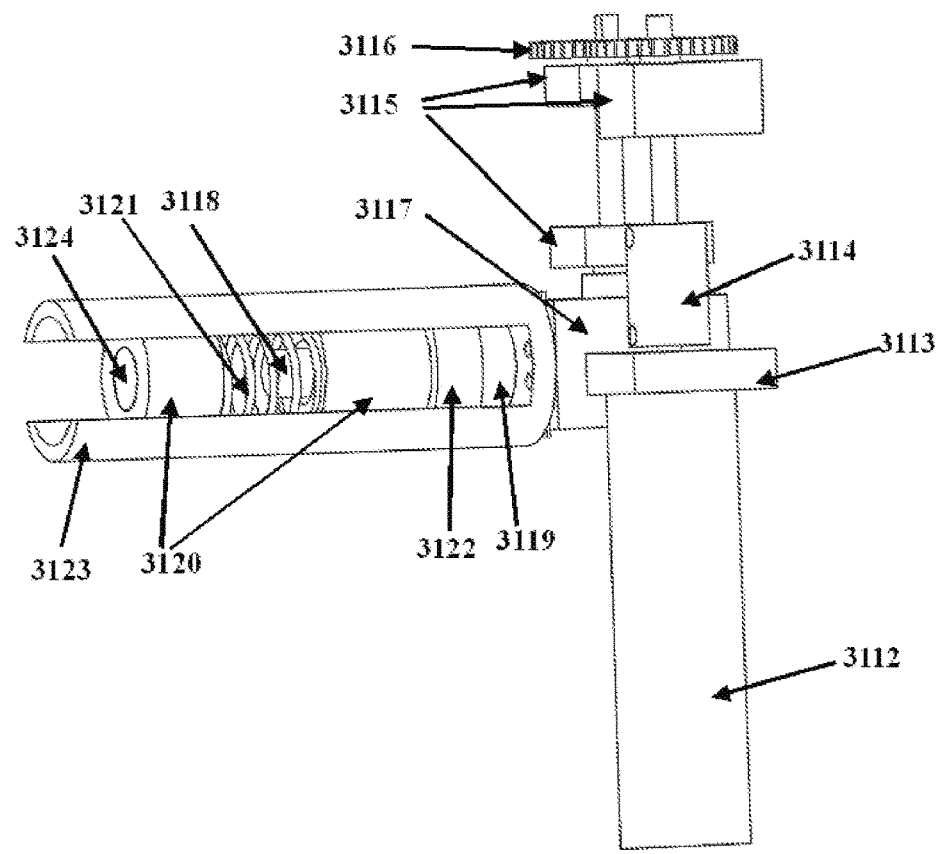
FIG. 9 is a structural schematic diagram of a surgical end effector driving mechanism in a driving unit according to an example of the present invention.

As shown in FIGS. 1, 7 and 9, the driving unit 30 may include a driving segment 301, a driving segment fixing disk 302, driving segment spacing disks 303, a driving segment base plate 304, a driving segment structural backbone 305, a first structural backbone guide channel 306, a feedback structural backbone 307, a potentiometer 308, a second fixing end plate 309, a structural backbone driving mechanism 310, and a surgical end effector driving mechanism 311.

The driving segment 301 may be of a thick and short ring structure from the driving segment fixing disk 302 to the driving segment base plate 304, and the number and length of the structural segment of the driving segment 301 can be consistent with the proximal structural segment II in the proximal structural body 13. The driving segment 301 is sheathed outside the proximal structural body 13, and the driving segment fixing disk 302 is externally sheathed over the proximal fixing disk 131 and can be quickly and securely connected thereto.

The driving segment base plate 304 is externally sheathed over the proximal base disk 134 and can be quickly and securely connected thereto.

The structural backbone driving mechanism 310 and the potentiometer 308 may be fixed onto the second fixing end plate 309. The structural backbone driving mechanism 310 is fixed outside the middle connecting body 12. The second fixing end plate 309 is externally sheathed over the first fixing end plate 121 and can be quickly and securely connected thereto. The number of the structural backbone driving mechanisms 310 can be consistent with the number of the driving segment structural backbones 305, and the number of the potentiometers 308 can be consistent with the number of the feedback structural backbones 307. One end of the first structural backbone guide channel 306 is fixedly connected to the structural backbone driving mechanism 310, and the other end thereof is fixedly connected to the driving segment base plate 304. The driving segment spacing disks 303 are distributed at intervals between the driving segment base plate 304 and the driving segment fixing disk 302. The middle section of the driving segment structural backbone 305 passes through the structural backbone driving mechanism 310, and two ends thereof respectively pass through the first structural backbone guide channel 306 and then pass through the driving segment base plate 304 and the driving segment spacing disk 303 in sequence, and are respectively fixed onto the driving segment fixing disk 302. The number of the driving segment structural backbones 305 in each of the driving segments 301 may be two or more (two in the present embodiment, and the present invention is not limited thereto). The driving segment spacing disks 303 function to prevent the driving segment structural backbone 305 from being destabilized when being pushed and pulled. The structural backbone driving mechanisms 310 implement the turning motion of the driving segment 301 in any direction by cooperatively pushing and pulling the driving segment structural backbones 305, thereby implementing the turning motion of the proximal structural body 13 in the same direction, and finally implementing the turning motion of the distal structural body 11 in the opposite direction.

A part of the feedback structural backbone 307 is arranged in the driving segment 301, and the number of the feedback structural backbones in each of the driving segments 301 may be two or more (two in the present embodiment, and the present invention is not limited thereto), and the number of the feedback structural backbones 307 must be consistent with that of the potentiometers 308. Two ends of the feedback structural backbone 307 are respectively fixed onto the driving segment fixing disk 302 and a slider in the potentiometer 308, and the turning motion of the driving segment 301 causes the change in length of the part of the feedback structural backbone 307 that is located in the driving segment 301. This change in length will cause the feedback structural backbone 307 to push and pull the slider in the potentiometer 308, such that the change in length is recorded by the potentiometer 308. Since the length of the driving segment 301 can remain unchanged, the length combination of the part of the feedback structural backbone 307 that is located in the driving segment 301 will uniquely determine the direction of a turning plane of the driving segment and a turning angle of same in the turning plane. Therefore, the absolute turned shape of the current driving segment 301 can be obtained by the potentiometer 308 and the feedback structural backbone 307, to achieve further closed-loop control of the driving segment. The potentiometer 308 is linked to the driving segment 301, can provide real-time feedback of the posture of the driving segment 301, and can assist the driving segment 301 to return to the initial posture in the event of a surgical system failure.

Figure 8A:
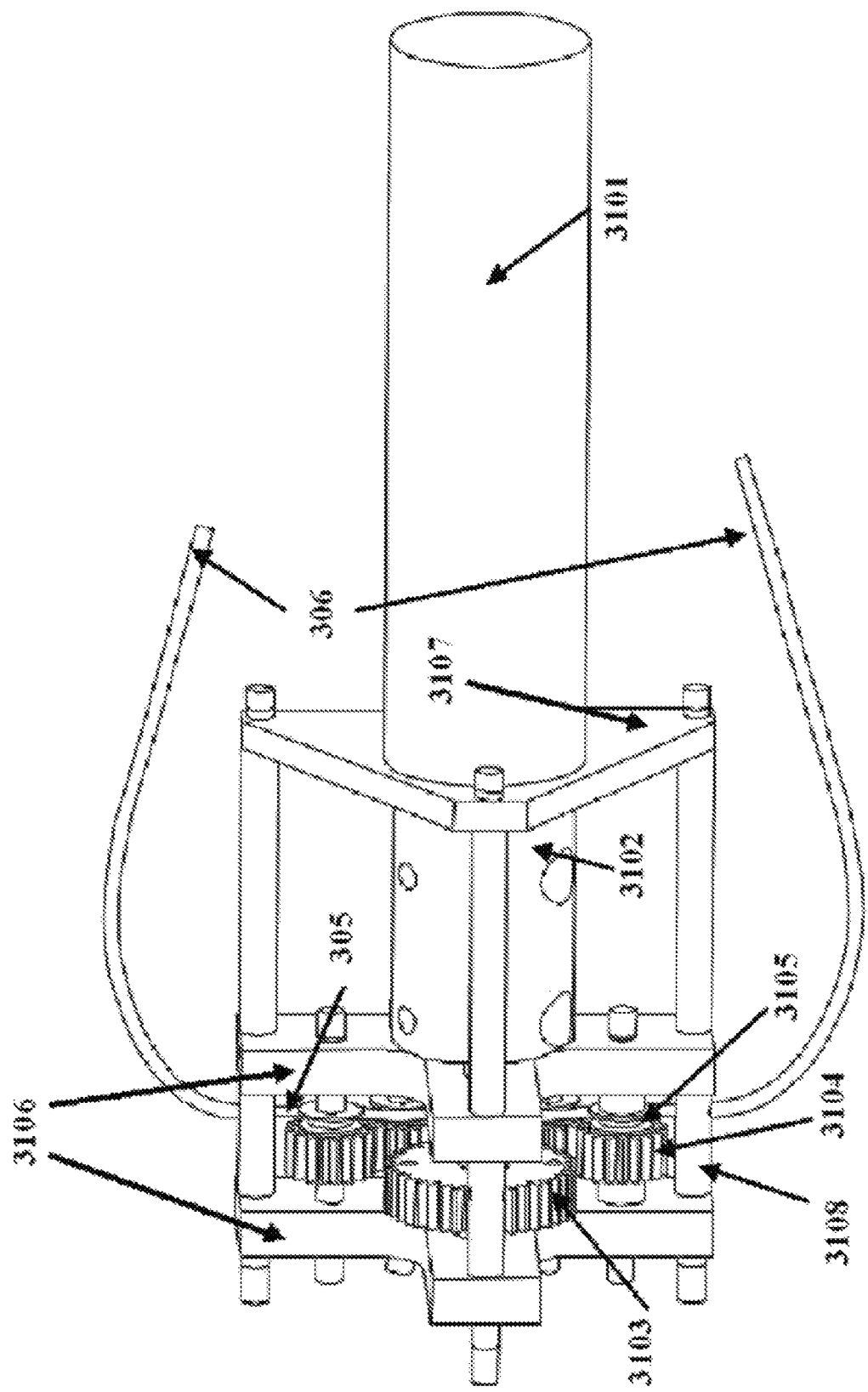
FIG. 8A is a structural schematic diagram of a structural backbone driving mechanism in a driving unit according to an example of the present invention.
Figure 8B:
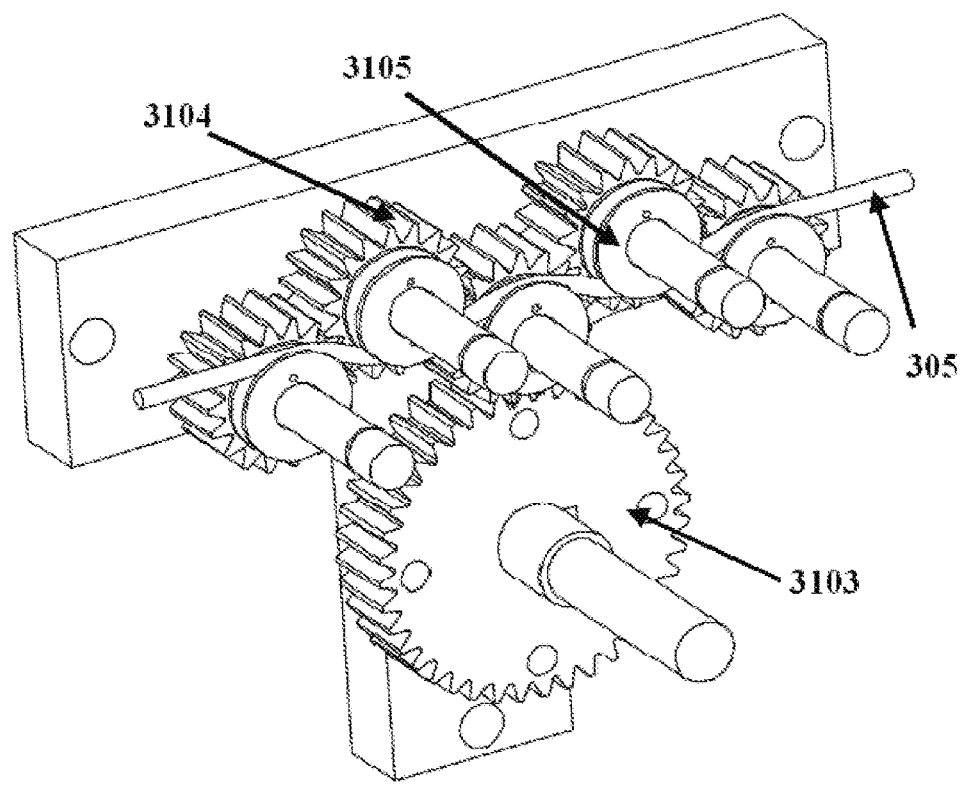
FIG. 8B is a partial schematic diagram of the structural backbone driving mechanism shown in FIG. 8A.

As shown in FIGS. 8A and 8B, the structural backbone driving mechanism 310 may comprise a structural backbone driving motor 3101, a first coupling 3102, a driving gear 3103, a set of transmission gears 3104, a set of pulleys 3105, driving support plates 3106, a first motor fixing plate 3107 and a support column 3108. Two driving support plates 3106 and the first motor fixing plate 3107 are arranged at intervals in sequence and are integrally connected via the support column 3108. The set of transmission gears 3104 and the set of pulleys 3105 are rotatably arranged between the two driving support plates 3106 and constitute several pulley-gear assemblies, respectively. The pulley and the gear of each of the pulley-gear assemblies are fixedly connected, and the gears mesh with each other. The driving gear 3103 is also rotatably arranged between the two driving support plates 3106 and connected to the structural backbone driving motor 3101 via the first coupling 3102. The driving gear 3103 meshes with the gear of one of the pulley-gear assemblies to transmit a driving force. The set of transmission gears 3104 and the set of pulleys 3105 rotate together about their respective axes, thereby pushing and pulling the driving segment structural backbone 305 by means of frictional forces. One end of the first structural backbone guide channel 306 is fixedly connected to the support column 3108. The driving segment structural backbone 305 extends between the pulleys of the pulley-gear assemblies through the first structural backbone guide channel 306 and generates local deformation under the extrusion of the pulleys, thereby generating relatively large frictional forces on contact faces with the pulleys.

It should be noted that the number, size and positional distribution of the pulley-gear assemblies can be adjusted according to the driving force required for the motion of the driving segment structural backbone 305 to ensure that the driving segment structural backbone 305 does not slip relative to the set of pulleys 3105 during the motion. In addition, since the driving unit comprises the set of pulleys and the driving segment structural backbone closely attached to surfaces of the set of pulleys and the driving segment structural backbone can generate local deformation in the set of pulleys, by driving the set of pulleys to rotate, the pushing and pulling of the driving segment structural backbone can be realized with an extremely compact structure.

As shown in FIGS. 1 and 9, the surgical end effector driving mechanism 311 may comprise a connection frame 3111, a surgical end effector driving motor 3112, a second motor fixing plate 3113, a second coupling 3114, a support plate 3115, a pair of transmission gears 3116, a bevel gear box 3117, a threaded rod 3118, a nut 3119, a sliding block 3120, a spring 3121, an anti-rotation slider 3122, a sliding groove jacket 3123 and a second magnet 3124.

The second motor fixing plate 3113, the support plate 3115 and the bevel gear box 3117 are all fixed onto the connection frame 3111 for fixing the surgical end effector driving motor 3112 and supporting shafts of an input gear and an output gear of the pair of transmission gears 3116. The input gear of the pair of transmission gears 3116 is coaxially fixed to the second coupling 3114, and the output gear of the pair of transmission gears 3116 is coaxially fixed to an input end of the bevel gear box 3117. The surgical end effector driving motor 3112 implements the rotation of the threaded rod 3118 by means of the second coupling 3114, the pair of transmission gears 3116 and the bevel gear box 3117. The sliding groove jacket 3123 is fixed onto the bevel gear box 3117.

The threaded rod 3118 is located within the sliding groove jacket 3123 and is coaxially fixed to an output end of the bevel gear box 3117. The nut 3119 is in threaded fit with the threaded rod 3118. There may be two sliding blocks 3120, which are arranged spaced apart from each other, and can slide back and forth within the sliding groove jacket 3123. The nut 3119 is fixedly coupled to one of the sliding blocks 3120 via the anti-rotation slider 3122. Under the action of the anti-rotation slider 3122, the threaded rod 3118 rotationally drives the nut 3119 and the sliding block 3120 to slide back and forth under the guidance of a lateral groove of the sliding groove jacket 3123. The second magnet 3124 is fixed to the front end of the other sliding block 3120, and can be coupled with the first magnet 206 in the transmission mechanism 202 to transmit a push-pull motion, thereby implementing the motion control of the surgical end effector 201. Two ends of the spring 3121 as an elastic element are fixedly connected to the two sliding blocks 3120 respectively, so that the nut 3119 can output a stable and controllable pushing or pulling force to the actuation wire 207 within a limited sliding travel, whereby the application of excessive pushing or pulling force to the actuation wire can be avoided and the generation of an excessive snap force by the surgical end effector 201 (such as surgical forceps) is prevented.

It can be seen, based on the above description, that the connection frame 3111, the second motor fixing plate 3113, the support plate 3115, the surgical end effector driving motor 3112 and the pair of transmission gears 3116 can together constitute a motor drive assembly. The output gear of the pair of transmission gears 3116 can be used as the output end of the motor drive assembly, which is coaxially fixed to the input end of the bevel gear box 3117. The threaded rod 3118, the nut 3119 and the anti-rotation slider 3122 can together constitute a linear transmission assembly. The nut 3119 is the movable end of the linear transmission assembly, which is securely connected to one of the sliding blocks 3120 via the anti-rotation slider 3122. In this way, the motor drive assembly can transmit power to the linear transmission assembly through the bevel gear box 3117 so that the linear transmission assembly can drive the sliding block connected thereto to slide back and forth under the guidance of the lateral groove of the sliding groove jacket. Consequently, the surgical end effector driving mechanism 311 in the driving unit 30 can drive the surgical end effector 201 at the front end of the distal structural body 11 to implement the action control of the surgical end effector 201.

In addition, the driving segment 301 can be quickly connected to the proximal structural body 13, and the transmission mechanism 202 can also be quickly connected to the surgical end effector driving mechanism 311. As an example, the quick connection function can be implemented using magnets. With this quick connection function, the flexible continuous body structure and the transmission mechanism can be quickly removed or replaced from the flexible surgical instrument.

Figure 10:
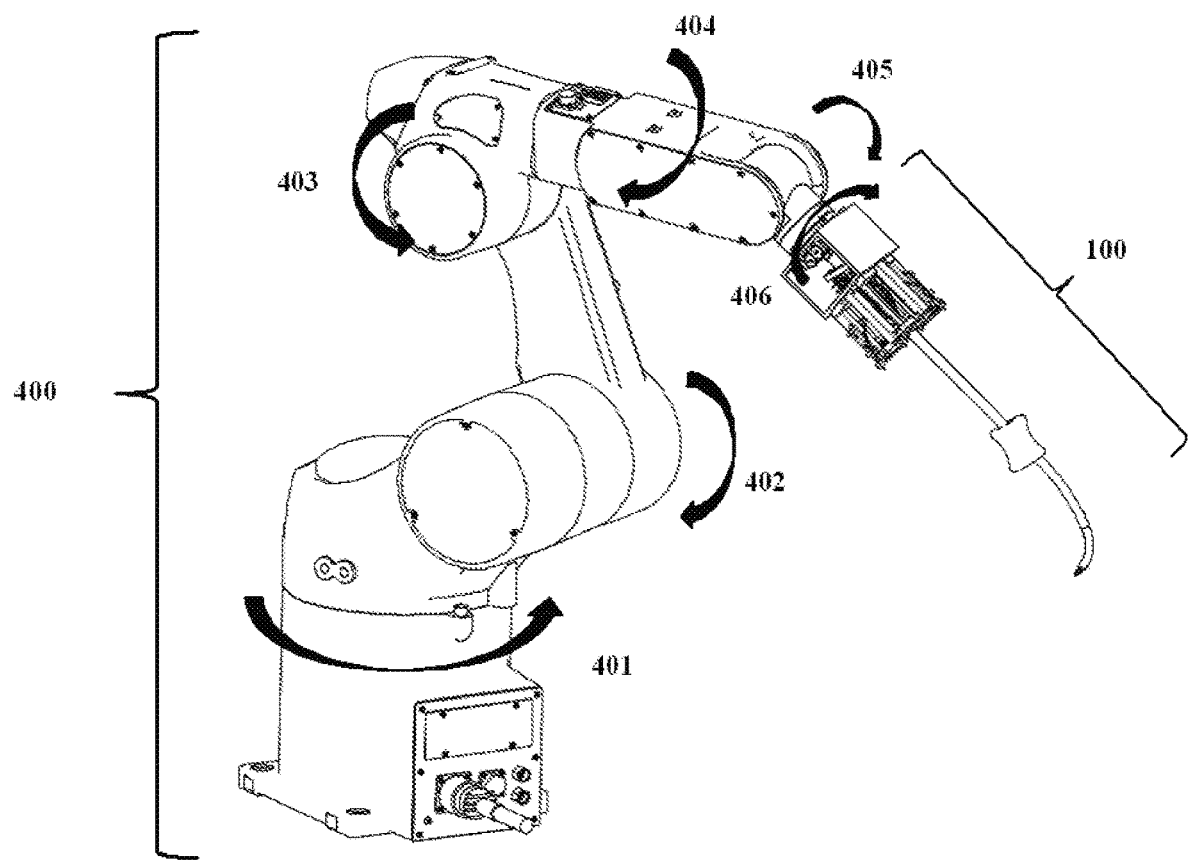
FIG. 10 is a schematic diagram of the implementation of a flexible surgical instrument connected to a multi-degree-of-freedom robotic arm in accordance with an example of the present invention.

FIG. 10 illustrates a schematic diagram of the implementation of a flexible surgical instrument 100 provided by the present invention being connected to a multi-degree-of-freedom robotic arm 400, the flexible surgical instrument 100 being fixedly mounted on an end disk of the multi-degree-of-freedom robotic arm 400 via the connection frame 3111. The multi-degree-of-freedom robotic arm 400 comprises six rotary joints 401-406, wherein the first five rotary joints 401-405 can implement the overall lateral rotation and the overall feed freedom of the flexible surgical instrument 100 with an abdomen entrance point as the fixed point, and the rotary joint 406 can implement the overall rotation freedom of the flexible surgical instrument 100 about its own axis. Consequently, the multi-degree-of-freedom robotic arm 400 enables a wide range of motions of the flexible surgical instrument 100, and the flexible surgical instrument 100 can realize a small range of precise and flexible motion of the distal structural body 11 in the body of the patient and the driving of the surgical end effector 201.

In one embodiment, as shown in FIG. 1, the distal structural body 11 is externally covered by a flexible envelope 40, and the envelope 40 can improve the appearance and insertion smoothness of the distal structural body 11.

In one embodiment, as shown in FIG. 2, the distal structural body 11 is further externally covered by a rigid outer sleeve 50, and the outer sleeve 50 illustrated in this embodiment is a rigid pre-bent sleeve. The outer sleeve 50 passes through a sheath 60 fixed to a skin incision, and the sheath 60 provides a channel for instruments (typically three surgical tools and one imaging illumination tool) required for the single-port laparoscopic surgery, wherein the channel may be an oblique channel and does not limit the lateral rotation motion of the surgical tool about a particular fixed point (the intersection point between an axis of the channel in the sheath 60 and the skin incision), so that the flexible surgical instrument 100 can perform the single-port laparoscopic surgery.

In another embodiment, as shown in FIG. 4, when the outer sleeve 50 illustrated in this embodiment is a rigid straight sleeve, it can pass through a sheath 60 containing only one channel, and the sheath 60 is also fixed to the skin incision. Multiple flexible surgical instruments 100 with multiple sheaths 60 can be used for performing multi-port laparoscopic surgery. It should be noted that the flexible surgical instrument 100 can adjust with the multi-degree-of-freedom robotic arm 400 the direction of the outer sleeve 50 and the distal structural body 11 therein and the distance by which same extend out of the sheath 60, further improving the motion performance of the distal structural body 11.

It should be understood by those skilled in the art that the single-channel sheath for the multi-port laparoscopic surgery shown in FIG. 4 and the multi-channel sheath for the single-port laparoscopic surgery shown in FIG. 2 are two parallel embodiments, and the two structural forms of the distal structural body 11 provided by the present invention can both be applied to the above two embodiments.

It should be noted that relational terms herein, such as first and second and the like, are used solely to distinguish one from another entity or action without necessarily requiring or implying any actual such relationship or order between such entities or actions. The terms "comprise," "include" or any variation thereof are intended to cover a non-exclusive inclusion, so that a process, method, article or apparatus that comprises a series of elements not only comprises those elements but may also comprise other elements not expressly listed or inherent to such a process, method, article, or apparatus. In the absence of more restrictions, the element defined by the phrase "comprising a . . . " do not preclude the presence of a further identical element in the process, method, article or apparatus that comprising the element.

The method and device provided in the embodiments of the present invention have been described in detail, the principle and implementation of the present invention have been illustrated with reference to the specific examples, and the above description of the embodiments is merely for the purpose of assisting in understanding the method of the present invention and its core concept. For a person skilled in the art, various changes could be made in the particular embodiments and the scope of application in accordance with the concept of the present invention. In summary, the contents of the description should not be construed as limiting the present application.

The invention claimed is:

1. A flexible surgical instrument, comprising:
   a distal structural body comprising at least one distal structural segment, the at least one distal structural segment comprising a distal fixing disk and structural backbones;
   a proximal structural body comprising at least one proximal structural segment, the at least one proximal structural segment comprising a proximal fixing disk, and structural backbones, the structural backbones of the distal structural segment being securely connected to or the same as corresponding structural backbones of the proximal structural segment; and
   a driving unit comprising:
      a driving segment comprising a driving segment fixing disk nested with the proximal fixing disk and operable to turn the at least one proximal structural segment;
      a driving segment structural backbone connected to the driving segment; and
      a structural backbone driving mechanism operable to drive the driving segment structural backbone to turn the driving segment;
   the flexible surgical instrument further comprising:
      a feedback structural backbone connected to the driving segment fixing disk; and
      a potentiometer to record length change of the feedback structural backbone.

2. The flexible surgical instrument of claim 1, wherein the driving segment comprises a driving segment spacing disk, and the driving segment structural backbone passes through the driving segment spacing disk and comprises a first end and a second end fixed to the driving segment fixing disk, and wherein the first end or the second end of the driving segment structural backbone extends through the structural backbone driving mechanism and turns back to the driving segment fixing disk.

3. The flexible surgical instrument of claim 1, wherein the driving segment comprises a driving segment base plate, and the driving segment structural backbone passes through the driving segment base plate and comprises a first end and a second end fixed to the driving segment fixing disk, and wherein the first end or the second end of the driving segment structural backbone extends through the structural backbone driving mechanism and turns back to the driving segment fixing disk.

4. The flexible surgical instrument of claim 3, wherein the driving segment further comprises:
   a first structural backbone guide channel connected to the driving segment base plate, and the driving segment structural backbone passes through the first structural backbone guide channel.

5. The flexible surgical instrument of claim 1, wherein the structural backbone driving mechanism comprises:
   a gear-pulley transmission mechanism connected to the driving segment structural backbone and operable to convert a first rotary motion into opposite linear motions of the first end and the second end of the driving segment structural backbone.

6. The flexible surgical instrument of claim 5, wherein the gear-pulley transmission mechanism comprises:
   a driving gear to transmit the first rotary motion;
   a first pulley-gear assembly comprising:
      a first gear meshing with the driving gear; and
      a first pulley coaxially and fixedly connected to the first gear, and
   the driving segment structural backbone is in a frictionally connection with circumferential side of the first pulley.

7. The flexible surgical instrument of claim 6, wherein the gear-pulley transmission mechanism comprises:
   a second pulley-gear assembly comprising:
      a second gear meshing with the first gear; and
      a second pulley coaxially and fixedly connected to the second gear; and
   a third pulley-gear assembly comprising:
      a third gear meshing with the first gear; and
      a third pulley coaxially and fixedly connected to the third gear, and
   the first pulley, the second pulley, and the third pulley are disposed at opposing sides of the driving segment structural backbone, and the driving segment structural backbone is in frictional connection with circumferential side of the second pulley, the first pulley, and the third pulley.

8. The flexible surgical instrument of claim 1, wherein a proximal end of the structural backbone of the at least one proximal structural segment is securely connected to the proximal fixing disk, and a distal end of the structural backbone of the at least one distal structural segment is securely connected to the distal fixing disk.

9. The flexible surgical instrument of claim 1, wherein:
   the at least one proximal structural segment further comprises a proximal spacing disk, the structural backbone of the at least one proximal structural segment passing through the proximal spacing disk; and
   the at least one distal structural segment further comprises a distal spacing disk, the structural backbone of the at least one distal structural segment passing through the distal spacing disk.

10. The flexible surgical instrument of claim 9, wherein:
    the distal structural body comprises a plurality of the distal structural segments or the proximal structural body comprises a plurality of the proximal structural segments, and
    the structural backbones of a preceding distal structural segment or proximal structural segment comprise elastic elongated tubes, the structural backbones of a next distal structural segment or proximal structural segment are able to pass through the elastic elongated tubes or directly pass through structural backbone passage holes in the distal spacing disk or in the proximal spacing disk, respectively.

11. The flexible surgical instrument of claim 1, wherein the at least one distal structural segment comprises a bellows, and the segment structural backbones of the at least one distal structural segment pass through the bellows.

12. The flexible surgical instrument of claim 1, wherein the at least one distal structural segment comprises:
   a first bellows and a second bellows, and the segment structural backbones of the at least one distal structural segment pass through the first and second bellows; and
   a bellows connection plate securely connected between the first bellows and the second bellows.

13. The flexible surgical instrument of claim 1, further comprising:
   a middle connecting body comprising:
      a first fixing end plate; and
      second structural backbone guide channels, and
   wherein the at least one proximal structural segment comprises a proximal base disk;
   wherein proximal ends of the second structural backbone guide channels are fixedly connected to the proximal base disk, and distal ends of the second structural backbone guide channels are fixedly connected to the first fixing end plate, and
   wherein the structural backbones of the at least one distal structural segment pass through the second structural backbone guide channels and distal ends of the structural backbones of the at least one distal structural segment are securely connected to the distal fixing disk.

14. The flexible surgical instrument of claim 1, further comprising:
   a surgical end effector disposed at a distal end of the distal structural body; and
   an actuation wire passing through the distal structural body, and the actuation wire comprising a proximal end securely connected to a transmission mechanism and a distal end securely connected to the surgical end effector.

15. The flexible surgical instrument of claim 14, wherein the transmission mechanism comprises:
   a guide block disposed between the distal structural body and the proximal structural body; and
   a connection block slidably passing through the guide block, and
   the proximal end of the actuation wire is securely connected to the connection block.

16. The flexible surgical instrument of claim 15, wherein the driving unit further comprises a surgical end effector driving mechanism; and
   the surgical end effector driving mechanism comprises:
   a linear transmission assembly to transmit a push-pull motion to the connection block.

17. The flexible surgical instrument of claim 16, wherein the linear transmission assembly comprises:
   a threaded rod to receive a second rotation motion; and
   a nut in threaded connection with the threaded rod and connected to the connection block.

18. The flexible surgical instrument of claim 17, wherein:
   the transmission mechanism further comprises a first magnet fixed to the connection block, and
   the surgical end effector driving mechanism further comprises a second magnet connected to the first magnet and the nut.

19. A flexible surgical instrument system, comprising:
   a flexible surgical instrument, comprising:
      a distal structural body comprising at least one distal structural segment, the at least one distal structural segment comprising a distal fixing disk and structural backbones;
      a proximal structural body comprising at least one proximal structural segment, the at least one proximal structural segment comprising a proximal fixing disk, and structural backbones, the structural backbones of the distal structural segment being securely connected in one-to-one correspondence to or the same as corresponding structural backbones of the proximal structural segment; and
      a driving unit comprising:
         a driving segment comprising a driving segment fixing disk nested with the proximal fixing disk and operable to turn the at least one proximal structural segment;
         a driving segment structural backbone connected to the driving segment; and
         a structural backbone driving mechanism operable to drive the driving segment structural backbone to turn the driving segment;
   the flexible surgical instrument further comprising:
      a feedback structural backbone connected to the driving segment fixing disk; and
      a potentiometer to record length change of the feedback structural backbone;
   a structural backbone driving motor operable to drive the structural backbone driving mechanism; and
   at least one robotic arm connected to the flexible surgical instrument.

* * * * *